US008765468B2

(12) United States Patent
Boyce

(10) Patent No.: US 8,765,468 B2
(45) Date of Patent: **\*Jul. 1, 2014**

(54) SURGICAL DEVICE FOR SKIN THERAPY OR TESTING

(71) Applicant: Steven T. Boyce, Cincinnati, OH (US)

(72) Inventor: Steven T. Boyce, Cincinnati, OH (US)

(73) Assignees: University of Cincinnati, Cincinnati, OH (US); Shriners Hospitals for Children, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/901,728

(22) Filed: May 24, 2013

(65) Prior Publication Data

US 2013/0259919 A1    Oct. 3, 2013

Related U.S. Application Data

(63) Continuation of application No. 12/818,302, filed on Jun. 18, 2010, now Pat. No. 8,450,108, and a continuation of application No. 10/092,237, filed on Mar. 6, 2002, now Pat. No. 7,741,116.

(51) Int. Cl.
*C12N 5/16* (2006.01)
*C12N 5/10* (2006.01)
*C12N 5/071* (2010.01)

(52) U.S. Cl.
USPC ........ 435/347; 435/397; 435/373; 424/93.21; 424/93.1

(58) Field of Classification Search
USPC ............... 435/347, 397, 373; 424/93.21, 93.1
See application file for complete search history.

(56) References Cited

U.S. PATENT DOCUMENTS

| | | | |
|---|---|---|---|
| 4,458,678 A | 7/1984 | Yannas et al. | |
| 4,673,649 A | 6/1987 | Boyce et al. | |
| 4,963,489 A | 10/1990 | Naughton et al. | |
| 5,273,900 A | 12/1993 | Boyce | |
| 5,443,950 A | 8/1995 | Naughton et al. | |
| 5,536,656 A | 7/1996 | Kemp et al. | |
| 5,622,862 A | 4/1997 | Squinto et al. | |
| 5,712,163 A * | 1/1998 | Parenteau et al. | 435/405 |
| 5,755,814 A | 5/1998 | Berg et al. | |
| 5,785,964 A | 7/1998 | Naughton et al. | |
| 5,858,721 A | 1/1999 | Naughton et al. | |
| 5,976,878 A | 11/1999 | Boyce | |
| 6,039,760 A | 3/2000 | Eisenberg | |
| 6,733,530 B1 | 5/2004 | Lam et al. | |
| 7,741,116 B2 * | 6/2010 | Boyce | 435/347 |
| 8,450,108 B2 * | 5/2013 | Boyce | 435/347 |
| 2002/0193875 A1 | 12/2002 | Amano et al. | |

FOREIGN PATENT DOCUMENTS

| | | |
|---|---|---|
| CN | 1363398 | 8/2002 |
| EP | 0 363 400 B1 | 3/1993 |
| JP | H05-500169 | 9/1993 |
| JP | 05-317406 | 12/1993 |
| JP | 2000-125855 | 5/2000 |
| JP | 2002-505859 | 2/2002 |
| WO | 91/16010 A1 | 10/1991 |
| WO | 95/19743 A1 | 7/1995 |
| WO | 97/41208 A1 | 11/1997 |
| WO | 97/41298 A1 | 11/1997 |
| WO | 98/22514 A1 | 5/1998 |
| WO | 99/43787 A2 | 9/1999 |
| WO | 99/45770 A1 | 9/1999 |
| WO | 00/27996 A1 | 5/2000 |
| WO | 01/92477 A2 | 12/2001 |

OTHER PUBLICATIONS

Boyce et al. (1996) "Skin repair with cultured cells and biopolymers" Chapter 15, Human Biomaterials Applications, Wise et al. Eds., pp. 347-377.*
Krejci et al. In Vitro Reconstitution of Skin: Fibroblasts Facilitate Keratinocyte Growth and Differentiation on Acellular Reticular Dermis. J. Invest. Dermol. 97 (1991) 843-848.
Hata et al. L-Ascorbic Acid 2-Phosphate Stimulates Collagen Accumulation, Cell Proliferation, and Formation of a Three-Dimensional Tissuelike Substance by Skin Fibroblasts. J. Cell Physiol. 138 (1989) 8-16.
International Search Report, PCT/US03/06479, mailed Jul. 23, 2003, 3 pages.
Boyce et al. Skin wound closure in athymic mice with cultured human cells, biopolymers, and growth factors. Surgery 110 (1991) 866-876.

(Continued)

*Primary Examiner* — Anne Marie S Wehbe
(74) *Attorney, Agent, or Firm* — Thompson Hine LLP

(57) ABSTRACT

A device, and method of making the device, capable of therapeutic treatment and/or for in vitro testing of human skin. The device may be used on skin wounds for burned, injured, or diseased skin, and provides structures and functions as in normal uninjured skin, such as barrier function, which is a definitive property of normal skin. The device contains cultured dermal and epidermal cells on a biocompatible, biodegradable reticulated matrix. All or part of the cells may be autologous, from the recipient of the cultured skin device, which advantageously eliminates concerns of tissue compatibility. The cells may also be modified genetically to provide one or more factors to facilitate healing of the engrafted skin replacement, such as an angiogenic factor to stimulate growth of blood vessels. The inventive device is easy to handle and manipulate for surgical transplant, can be made into large sheets to minimize the number of grafts required to cover a large surface area to be treated, and can be produced within the time frame to treat a burned individual requiring a skin graft.

28 Claims, No Drawings

(56) References Cited

OTHER PUBLICATIONS

Partial European Search Report, dated Jan. 27, 2011, mailed Feb. 9, 2011, 11 pages.
Japanese Patent Office Non-Final Office Action dated Jan. 25, 2011 regarding application JP2008-101712, Surgical Device for Skin Therapy or Testing.
Boyce. Pigmentation and Inhibition of Wound Contraction by Cultured Skin Substitutes With Adult Melanocytes After Transplantation to Athymic Mice, Journal of Investigative Dermatology 100 (1993) 360-365.
Munster et al. Acellular allograft dermal matrix: immediate or delayed epidermal coverage, Journal of the International Society for Burn Injuries 27 (2001) 150-153.
Middelkoop et al. Adherence, proliferation and collagen turnover by human fibroblasts seeded into different types of collagen sponges, Cell and Tissue Research, Berlin, DE, 280, (1995) 447-453.
Compton et al. Organized skin structure is regenerated in vivo from collagen-gag matrices seeded with autologous keratinocytes, Journal of Investigative Dermatology 10 (1998) 908-916.
Maruguchi et al. A new skin equivalent: keratinocytes proliferated and differentiated on collagen sponge containing fibroblasts, Plastic and Reconstructive Surgery 93 (1994) 537-546.
Thomson Scientific London, GB, Stratified artificial skin chitosan or its derivative as matrix clathrum, (Aug. 2002) Abstract.
US-FDA OrCeITM Bilayered Cellular (Aug. 2001) Retrieved from Internet: http://www.fda.gov/MedicalDevices/Prod_uctsandMedicalProcedures/DeviceApprovalsandlearances/Recently-ApprovedDevices/ucm085369.htm Retrieved on Jan. 19, 2011).
Furukawa et al. Tissue-engineered skin using aggregates of normal human skin fibroblasts and biodegradable material, J Artif Organs 4 (2001) 353-356.
Labitzke. A serum-free medium formulation supporting growth of human umbilical cord vein endothelial cells in, Cytotechnology 35 (2001) 87-92.
Extended European Search Report in family application EP10012359.5, mailing date May 3, 2011, 18 pages.
Spect. Comparative investigations to evaluate the use of organotypic cultures of transformed and native dermal and epidermal cells for permeation studies, European Journal of Pharmaceutics and Biopharmaceutics 46 (1998) 273-278.
Formanek et al. Optimized growth medium for primary culture of human oral keratinocytes, International Journal of Oral and Maxillofacial Surgery 25 (1996) 157-160.
Kim et al. Cellular artificial skin substitute produced by short period simultaneous culture of fibroblasts and keratinocytes, British Journal of Plastic Surgery 52 (1999) 573-578.
Naughton. From Lab Bench to Market Critical Issues in Tissue Engineering. N.Y. Acad. Sci. 961 (2002) 372-385.
Wilkins et al. Development of a Bilayered Living Skin Construct for Clinical Applications. Biotech and Bioeng. 43 (1994) 747-756.
Supp et al. Human dermal microvascular endothelial cells form vascular analogs in cultured skin substitutes after grafting to athymic mice. The FASEB Journal 16 (2002) 797-804.
Boyce. Design Principles for Composition and Performance of Cultured Skin Substitutes. Burns 27 (2001) 523-533.
Partial European Search Report, EP09004333, mailed May 25, 2009, 9 pages.
International Search Report, PCT/US03/06584, mailed Nov. 9, 2003, 6 pages.
Boyce et al. Structure of a collagen-GAG dermal skin substitute optimized for cultured human epidermal keratinocytes. J. Biomedical Materals Research 22 (1988) 939-957.
Boyce et al. Reconstructed skin from cultured human keratinocytes and fibroblasts on a collagen-glycosaminoglycan biopolymer substrate. Skin Pharmacology 3 (1990) 136-143.
Boyce. Cultured skin substitutes: a Review. Tissue Engineering 2 (1996) 225-266.
Harriger et al. Glutaraldehyde crosslinking of collagen substrates inhibits degradation in skin substitutes grafted to athymic mice. J. Biomedical Research 35 (1997) 137-145.
Boyce. Cultured skin for wound closure. Skin Substitute Production by Tissue Engineering: Clinical and Fundamental Applications, M. Rouabhia Ed. (1997) 75-102.
Boyce. Skin substitutes from cultured cells and collagen-GAG polymers. Medical and Biological Engineering and Computing (1998), 791-800.
Dagalakis et al. Design of an artificial skin. Part III. Control of pore structure. J. Biomedical Materials Research 14 (1980) 511-528.
Yannas et al. Design of an artificial skin. II. Control of chemical composition. J. Biomedical Materials Research 14 (1980) 107-131.
Yannas et al. Design of an artificial skin. I. Basic design principles. J. Biomedical Materials Research 14 (1980) 65-81.

* cited by examiner

SURGICAL DEVICE FOR SKIN THERAPY OR TESTING

This application is a continuation of U.S. patent application Ser. No. 12/818,302 filed Jun. 18, 2010, now U.S. Pat. No. 8,450,108, which is a continuation of U.S. patent application Ser. No. 10/092,237 filed Mar. 6, 2002 now U.S. Pat. No. 7,741,116, each of which is expressly incorporated by reference herein in its entirety.

This invention was made with government support under Grant Nos. GM050509 and FD-R-000672 awarded by the National Institutes of Health and the Food and Drug Administration, respectively.

FIELD OF THE INVENTION

The invention is directed generally to a surgical device for therapeutic treatment of skin wounds in a patient or testing of skin anatomy or physiology, and a method to prepare the device.

BACKGROUND

Skin is one of the largest organs in the body and covers substantially the entire outer surface of the body. Skin is composed of two main layers: the surface epithelium or epidermis, which contains keratinocytes
as one type of epidermal cells, and the subjacent connective tissue layer or dermis, which contains fibroblasts as one type of dermal cells. The functions of skin include protecting an organism from injury and dessication by serving as a barrier to infection, perceiving or detecting environmental stimuli, excreting various substances, regulating body temperature, and helping to maintain water balance. Because of its quantitative and qualitative importance, substantially intact and healthy skin is important, not only for the well being of an organism but for its very survival.

The health and integrity of skin may be compromised by congenital or acquired pathologic conditions, either acute or chronic, for which normal skin regeneration and repair processes may be inadequate. These conditions include burns, wounds, ulcers, infections, diseases and/or congenital abnormalities. Patients who are burned over a large surface area often require immediate and extensive skin replacement. Less life-threatening but chronic skin conditions, as occur in venous stasis, diabetic or decubitus ulcers as three examples, may progress to more severe conditions if left untreated, particularly because patients with these conditions have an underlying pathology. Reducing the morbidity and mortality in such patients depends upon timely and effective restoration of the structure and function of skin.

Skin substitutes derived either ex vivo or in vitro may be used to treat these or other conditions. Desirable properties of skin substitutes are ready availability, a minimum requirement for donor skin, relative simplicity to produce, and cost-effectiveness of fabrication and use. Several approaches to fabrication of skin substitutes which satisfy some or all of these requirements have been attempted, with varying degrees of success. However, no skin substitute has yet regenerated all of the structures and functions of skin. Rather, all are subsets of uninjured skin. Only a transplant of full thickness skin restores virtually all the structures and functions of normal uninjured skin, but furthermore, scars during healing.

Materials have been manufactured for therapeutic use in skin repair. These materials contain different components replacing or substituting the structures and functions of the dermis and/or epidermis. Examples of these materials include EpiCel™, which lacks a dermal component and uses the patients own cultured keratinocytes; Integra™, which uses a collagen-glycosaminoglycan (GAG) matrix to provide an acellular dermal component and uses a thin autograft; AlloDerm™ and a thin autograft; DermaGraft™, which uses a polyglycolic acid/polylactic acid (PGA/PLA) matrix and allogeneic human fibroblasts for the dermis; Hyaff/LaserSkin™, which uses hyaluran and fibroblasts for the dermis, and hyaluran and the patients own keratinocytes for the epidermis; and PolyActive™, which uses polyethylene oxide/polybutylthalate (PEO/PBT) and may use the patient's own fibroblasts for the dermis, and the patient's cultured keratinocytes for the epidermis.

Materials to either temporarily cover wounds, or to stimulate permanent skin repair processes, include ApliGraft™, which uses collagen gel and allogeneic fibroblasts for the dermis, and cultured allogeneic keratinocytes for the epidermis; Comp Cult Skin™ or Orcel™ which uses collagen and allogeneic fibroblasts for the dermis, and cultured allogeneic keratinocytes for the epidermis; and TransCyte™ fibroblasts for the dermis and a synthetic material, BioBrane™, for the epidermis.

While the above materials are useful to varying degrees, each has disadvantages and limitations. Some of the materials are fragile mechanically, making it difficult to perform the required manipulations and transfers of the material in large sections without tearing. Instead, the materials must be used as smaller pieces, which makes coverage of large surface areas technically laborious for the physician and cosmetically undesirable for the patient due to scarring where grafts adjoin. The materials are also susceptible to microbial contamination, which is unacceptable for patients who are already at an increased risk for infection due to their compromised conditions. The materials show varying rates of engraftment and times to heal, both of which must be considered in selecting the advantages of a particular material over another for a particular patient. For example, a material which is otherwise acceptable but which takes longer to engraft and heal is less desirable, because a successful recovery includes as rapid a return to a normal routine as possible.

The inventor's own previous composite skin replacement, disclosed in U.S. Pat. No. 5,976,878, which is expressly incorporated by reference herein in its entirety, had been successfully used for therapeutic treatment of skin wounds. It was applied surgically in a single procedure, and contained a layer of cultured epidermal cells, an acellular polymeric dermal membrane component, and a substantially nonporous lamination layer on one surface of the dermal membrane component. The dermal membrane component was formed from collagen, or collagen and a mucopolysaccharide compound, and was laminated with the same collagen-, or collagen and mucopolysaccharide-containing solution with a volatile cryoprotectant. The substantially nonporous lamination layer may be located between the dermal component and the layer of cultured epidermal cells, promoting localization of epidermal cells on the surface of the dermal component and movement of nutrients to the cells of the cellular epidermal component. This composition can also be used to deliver biologically active molecules to the site where it is applied.

Desirable features of the above-described composite skin replacement included a more rapid rate of vascularization of the area covered by the material, decreased microbial contamination, increased nutrient supply, and improved epidermal barrier function, compared to other materials. Areas covered with the composite skin replacement required less time to engraft and heal, and the material was less susceptible to microbial contamination than reported for other materials.

Other desirable features are that this material was relatively non-fragile and easy to handle, and could be generated relatively rapidly, for example, within the time frame in which a burn patient requires skin grafts. However, while no other alternative material has healed excised, full-thickness wounds more rapidly, and with as low an incidence of microbial contamination, limitations still exist. Thus, there remains a need to more closely approach structural and functional properties of normal uninjured skin.

SUMMARY OF THE INVENTION

The invention is directed to a device for surgical grafting of skin wounds, or for a model of skin in vitro and in animals. The device has an acellular, biocompatible, reticulated protein- or polypeptide-containing matrix to provide an attachment substrate for one or more layers or populations of cultured dermal and/or epidermal cells. The protein can be naturally occurring or synthetic and may be less than a full protein, for example, it may be a polypeptide. In various embodiments, cells used to populate the matrix may be from the recipient (autologous), another human (allogeneic), from another species (xenogeneic), or from multiple sources (chimeric). The epidermal cells include keratinocytes, melanocytes, immunocytes, and/or stem cells. The dermal cells include fibroblasts, endothelial cells, immunocytes, nerve cells, myocytes, and/or stem cells. Either or both of the epidermal and dermal cells may be genetically modified.

The invention is also directed to a method to prepare a device for surgical grafting of skin wounds, or for a model of skin in vitro and in animals. To a matrix on an absorbent substrate, a cell suspension is provided to deliver cells to the matrix for attachment. The inoculated matrix is incubated under conditions sufficient to result in a cellular device.

The device may also be used on a non-wounded surface, a minimally wounded surface, or a surgically prepared surface not requiring skin grafting, but for which the cells of the skin substitute may be bioengineered to provide a physiologic factor lacking in the recipient. Such a factor may be a protein, for example, insulin or coagulation Factor VIII, and may be provided, respectively, to a diabetic or hemophiliac patient having a deficiency of that protein.

Besides its use as a skin substitute, the inventive device can also be used as a living substrate on which to perform toxicological or other tests on various topically applied compounds, such as drugs, cosmetics, moisturizers, lotions, environmental toxins, industrial chemicals, etc. The device, containing cells from a particular individual, can show an individualized response to a variety of compounds. Such an approach may be useful to test the toxicity of skin contact compounds. The device may also be useful as a medical diagnostic tool to test individuals with allergies, or who exhibit dermal reactions to components found in pharmaceutical or over-the-counter products. In this embodiment, the device will reduce or eliminate in vivo toxicity testing.

These and other features of the invention will be appreciated with reference to the following detailed description.

DETAILED DESCRIPTION

The inventive, surgically-applied device for treatment of skin wounds is a matrix which supports dermal cells and/or epidermal cells. More particularly, an acellular biocompatible reticulated matrix is used as a support or scaffold to which cultured cells are applied, attach, and proliferate. In one embodiment, a reticulated protein matrix supports a continuous layer or population of cultured dermal cells, and an overlying layer or population of cultured epidermal cells. After incubating the inoculated matrix under conditions facilitating cell growth, the device is transplanted surgically to the patient. In one embodiment, transplantation may be performed within one day (about 16 hours to about 24 hours) after epidermal cell inoculation of the matrix. In another embodiment, transplantation may be performed within one month after epidermal cell inoculation of the matrix. Within these times, the device develops properties preferred for a therapeutic skin graft material. The use of cultured cells to form the material, in contrast to tissue obtained by conventional harvesting of split thickness skin with a dermatome, provides the advantage of much larger numbers of epidermal and dermal cells than by conventional harvesting, and thereby greatly reduces the requirement for donor skin to complete closure of extensive, full-thickness skin wounds.

Once the device is grafted to the patient, the biodegradable matrix is absorbed by the body. The cells organize to form functional skin tissue, referred to as an engrafted cultured skin substitute. The device has many of the properties and structures that are found in normal, uninjured skin, and functions as does normal, uninjured skin to protect the individual from fluid loss and microbial infection. For example, the device functions as an epidermal barrier, which is definitive of normal skin function as known to those skilled in the art. The device establishes a basement membrane, and maintains the same anatomic configuration of the cellular layers or populations as in normal, uninjured skin. The device produces and releases angiogenic factors and mediators of the inflammatory process, as does normal, uninjured skin. The device is effectively vascularized in less than one week, and becomes partially vascularized within two days after transplant.

In another embodiment of the invention, the device is used as a temporary skin substitute. In this embodiment, the matrix may be populated with cells having non-autologous genotypes. For example, cultured epidermal and/or dermal cells may be autologous, that is, obtained from the individual who is the intended recipient of the device and which can be used in a permanently engrafted device. In other embodiments, the epidermal and/or dermal cells may be allogeneic, that is, obtained from a human other than the recipient. In yet other embodiments, the epidermal and/or dermal cells may be xenogeneic, and obtained from a non-human animal, such as porcine epidermal and/or dermal cells to take advantage of the similarity of features and characteristics in pig skin in comparison to human skin. Xenogeneic cells may also be obtained from plants or microbes. The use of different sources for epidermal cells and/or dermal cells results in a genetically chimeric device. Regardless of the source of epidermal and/or dermal cells, one or more cells may be modified genetically. Various factors may affect the selection of particular genotypic compositions of the cells. For example, the use of allogeneic or xenogeneic cells may shorten the preparation time of the device, or may further reduce the requirement for donor skin from the patient. Depending upon the particular condition of the recipient, these factors may be an important determinant.

If skin cells from the patient to be treated with the inventive device are used, they are obtained from a biopsy of a healthy area of the patient's skin, using techniques known to one skilled in the art including punch biopsy, shave biopsy, and full thickness skin excision with suture closure. The dermal and epidermal cellular components are then separated and isolated into dermal cells and epidermal cells, as described by Boyce and Ham in *J. Tissue Culture Methods* 1985;9:83, and chapter 13 in *In Vitro Models for Cancer Research*, Vol. 3, p. 245, Webber and Sekely, Eds. CRC Press, Boca Raton Fla.

(1986), both of which are expressly incorporated by reference herein. The dermal and epidermal cells are individually cultured, as described by Boyce and Ham in *J. Invest. Dermatol.* 1983;81:335, and chapter 28 in *Methods in Molecular Medicine*, Vol. 18, p. 365, Morgan & Yarmush, Eds., Humana Press, Totowa N.J. (1998), both of which are expressly incorporated by reference herein.

Various cells in the epidermis, for example, keratinocytes, melanocytes, immunocytes, stem cells, or others, and various cells in the dermis, for example, fibroblasts, endothelial cells, immunocytes, nerve cells, myocytes, stem cells, or others, may be cultured either individually or collectively. After adequate cell numbers are obtained, or a specific cellular physiology is expressed, the cellular populations are harvested for subsequent population of the matrix. In various embodiments, the ratio of epidermal to dermal cells used to inoculate the matrix is in the range of about 2:1 or 1:1, but other cell ratios are also included.

Depending upon the application for which the device is prepared, selected types of epidermal cells and/or dermal cells may be included or excluded. As one example, a device may include melanocytes to restore pigmentation in the transplant site, Restoration of skin pigmentation is defined as any increase in the anatomic or physiologic function of skin color of the graft, although the extent of color may be more or less than in uninjured skin. As another example, a cultured skin composition may include endothelial cells to stimulate formation of blood vessels.

In preparing the device, any biocompatible material that is permissive as a substrate for culture and transplantation of cultured cells may be used. A full length natural or synthetic protein may be used, or a polypeptide may be used. One embodiment uses a freeze-dried sponge of collagen, either alone or in combination with a carbohydrate (a mucopolysaccharide, such as a glycosaminoglycan (GAG), particularly chondroitin-6-sulfate). The collagen may be bovine skin collagen, bovine tendon collagen, collagen from other tissue sources (e.g. bone, muscle), other xenogeneic sources (e.g. pig, sheep, goat, etc.), genetically engineered sources, human sources, or a combination of any of the above. Other proteins such as elastin or reticulin, or polymers of amino acids, whether naturally occurring or synthetic, may be used.

In one embodiment of preparing the matrix, a coprecipitate of collagen-GAG is cast, frozen, and dehydrated to form a reticulated matrix. This matrix is subsequently sterilized, rehydrated, and laminated by inoculation with cultured dermal and epidermal cells. Inoculation is performed at ambient humidity (room air) and the inoculated matrix is incubated in an atmosphere with saturated or reduced humidity. The matrix is then incubated, either submerged in a medium or with the matrix contacting a gaseous atmosphere. In the latter embodiment, the inoculated cells are on the atmospheric surface of the matrix. Each of these steps is now described in further detail.

Matrix-Forming Protein-Containing Fluid

A dispersion of collagen is prepared by presolublizing collagen (6.42 mg/ml) acetic acid (0.01 M to 1.0 M), usually for up to sixteen hours, after which the dispersion is stored at 4° C. A coprecipitate with a glycosaminoglycan (GAG), such as chondroitin-6-sulfate, may then be prepared if a carbohydrate is to be added. Chondroitin-6 sulfate (3.45 mg/ml) is added to acetic acid (0.01 M to 3.0 M).

The previously prepared collagen dispersion is redispersed for at least five minutes and transferred to a stainless steel insulated beaker with a recirculating refrigerated jacket. The GAG solution is added to the protein solution by any means which will produce an adequate agitation and shear to form a co-precipitate. This can be done by transferring the GAG solution to a drip bottle and adding the GAG to the collagen using a drip set to which a 22 gauge needle is attached, allowing the GAG solution to drip into 750 ml of the collagen dispersion, being mixed at a speed of 5,000 revolutions per minute (rpm) and maintained at 4° C., at a rate of one drop per ten seconds. After the entire volume of GAG has dripped into the collagen, the collagen-GAG coprecipitate is transferred to bottles and centrifuged to remove trapped air bubbles. The froth that collects on top is removed by aspiration, and the collagen-GAG coprecipitate is then collected.

Preparation of Crosslinked Matrix

The protein-containing fluid, with or without carbohydrate, is prepared to form the matrix. As preliminary steps, a lyophilizer (freeze-drying) apparatus is pre-chilled to about −35° C. to about −50° C. In one embodiment, a freezing bath is prepared in a high density polyethylene (HDPE) container containing 95% ethanol that has been pre-chilled at about −45° C. for at least four hours. However, any type of apparatus or configuration may be used which will remove heat at a controlled rate so that a drop in temperature, sufficient to freeze the matrix, occurs within a time frame of up to about four hours. For example, the time and temperature may be regulated to bring about a temperature drop from about 4° C. to about −40° C. within about two hours, or a temperature drop from about 4° C. to about −75° C. within about four hours.

The protein solution is introduced into an apparatus, more fully described in U.S. patent application Ser. No. 10/091, 849, now U.S. Pat. No. 6,905,10 entitled "Apparatus for Preparing a Biocompatible Matrix" filed on Mar. 6, 2002, which is expressly incorporated by reference herein in its entirety. The result is a matrix with a composition, structure, and properties which support the cultured dermal and epidermal cells to promote formation of the device.

Briefly, a matrix-forming solution is contained between two plates of a thermally conductive material, with a gasket forming the remaining sides of a sealed chamber. The thickness of the gasket, in the range of about 0.1 mm to about 10 mm, regulates the thickness of the resulting matrix. The protein solution is introduced into the chamber. When the entire volume of solution has been added, the chamber is reversibly sealed, for example, by clamping. The chamber is then exposed to temperatures and/or conditions sufficient to remove heat at the previously-described, controlled rate to solidify the matrix.

After the matrix has solidified, the plates are separated to expose the frozen matrix. A plate containing the matrix is transferred to a refrigerated (−45° C.) shelf of a lyophilizer. Vacuum is then applied and, when the pressure is less than 60 mT, heat is also applied (30° C.). Lyophilization occurs overnight to a final vacuum of less than 15 mT. The freeze-dried matrix detaches spontaneously and is then transferred to a supporting sheet.

The matrix is cross-linked in the absence of a chemical crosslinking agent. This desirably eliminates any possible toxicity associated with residual chemical crosslinking agents, which may not be completely removed even after repeated washings. In one embodiment of the invention, thermal crosslinking is used. This is achieved by thermal dehydration in a vacuum oven (Lab-Line 3628) at about −100 kPa at about 105° C. for about 24 hours. Once crosslinking has occurred, the matrix is then stored in a desiccator at room temperature, either on a foil sheet or on other support material, for up to about three months.

The crosslinked matrix has a thickness of three millimeters or less. In various embodiments, and depending upon other factors such as a desired site of implantation, the crosslinked matrix has a thickness in the range of about 0.1 mm to about 1.0 mm, about 0.1 mm to about 2.0 mm, or about 0.1 mm to about 3.0 mm. A matrix having a thickness in the range of about 0.1 mm to about 1.0 mm, when inoculated with cells as described, results in a device having a thickness in the range of about 50 µm to about 500 µm. When such a device is used to treat skin wounds, this thickness desirably promotes rapid vascularization, nutrient delivery, population of the device with cells, and waste removal, and desirably facilitates degradation of the matrix after transplant, leaving only the cellular components of the composition remaining.

The cross-linked matrix is then cut into desired sizes and/or shapes. In one embodiment, it is cut into squares (for example, 9 cm×9 cm, 11 cm×11 cm, or about 19 cm×19 cm) using a straight edge and scissors. The matrix is packaged in a sterilization pouch (for example, Self-Seal™), and stored at room temperature in a desiccator for up to about three months.

The matrix is sterilized before inoculation, for example, by gamma irradiation at a dose of at least about 2.5 MRad (for example, SteriGenics, Westerville Ohio). Once sterilized, the matrix sterilization pouch is stored at room temperature in a desiccator for up to about one year.

Cellular Inoculation of the Matrix

All solutions are sterile filtered through a 0.22 µm filter, and all procedures are performed using aseptic techniques, as known to one skilled in the art.

The matrix is transferred to a container of any shape that will hold a volume of about 250 µl/cm$^2$ of matrix/incubation. The matrix is rinsed three times, for thirty minutes each rinse, with Hepes-buffered saline (HBS) solution, and two times for thirty minutes each with Dulbecco's Modified Eagle's medium (DMEM) solution or other suitable solution, as known to one skilled in the art.

After the final rinse, the medium is aspirated from the container and an inoculation frame is placed over the surface of the matrix. The inoculation frame is a square or rectangular frame made from a material that is chemically unreactive (e.g., stainless steel, Teflon™), under physiologic conditions (i.e., 37° C., saturated humidity, neutral pH, isotonic solutions). The frame is sufficiently massive (e.g., several ounces) to generate a seal to the movement of cells that are inoculated within its perimeter. The seal may be increased by addition of a bevel on the side contacting the matrix to increase the mass/area ratio, but with a sufficient amount of flat or rounded surface contacting the matrix to prevent cutting of the matrix. About 10-12 ml of supplemented DMEM, as will be described, is placed into the frame. The matrix and frame, containing supplemented DMEM, are permitted to equilibrate at 37° C./5% $CO_2$ for at least fifteen minutes before inoculating the matrix with cells.

Cells may be inoculated either submerged or emerged into the rehydrated matrix. In one embodiment, termed "submerged inoculation", cells are inoculated on a matrix submerged in medium. Culture medium without cells is added to the culture vessel outside of the inoculation frame to assure a secure seal, evidenced by no leakage of the medium from outside to inside the frame. After the preparation of a cell suspension by trypsinization of cells from selective cultures, dermal cells are inoculated at a density in the range of about 0.05–1.0×10$^6$ cells/cm$^2$. Subsequently, after the dermal cells have attached, epidermal cells are inoculated as suspensions and permitted to attach to the layer or population of dermal cells. Alternatively, combinations of dermal and epidermal cells may be inoculated simultaneously. The ratio of dermal cells to epidermal cells may be in the range of about 2:1 to about 1:1, but other ratios may be used. In other embodiments, dermal cells alone or epidermal cells alone may be inoculated.

The inoculation frame remains in place for about 12-48 hours after inoculation of the last cells onto the matrix. The inoculation frame is then removed, the edges of the matrix without cells are excised, and the inoculated surface of the matrix is exposed to the air to stimulate organization of the epidermal cells and the formation of an epidermal barrier. Before removing the inoculation frame, Dulbecco's Modified Eagle's medium with permissive supplements is used. After removing the frame and exposing the matrix to air, the medium is supplemented with progesterone and epidermal growth factor.

In another embodiment, termed "lifted inoculation", cells are inoculated on a matrix emerged from the culture medium. In this embodiment, the matrix is rehydrated and placed onto an absorbent substrate, with the upper surface contacting the atmosphere. The suspension of dermal cells is inoculated onto the matrix, and the drainage of the medium delivers the cells to the surface of the matrix, after which they attach. Simultaneously, or after up to one week, a suspension of epidermal cells is inoculated onto the matrix.

More specifically, a sterile, non-adherent, porous membrane (e.g., medical grade mesh (N-Terface7, Winfield Laboratories, Inc., Dallas Tex.); Teflon™; Millipore or Whatman filters of polyethersulfone, polyvinylidene fluoride, mixed cellulose ester, etc., hereinafter referred to as a porous membrane) is placed into a sterile tissue culture dish with HBS, and the sterile matrix is placed on top of the porous membrane and rehydrated. A sterile, absorbent material (e.g., Merocel™ that is 9 mm thick and of intermediate density (CF 100); cotton, gauze, etc., hereinafter referred to as an absorbent material) is placed into a second sterile dish to which excess DMEM is added. The dish is returned to the incubator to equilibrate.

Preparatory to inoculating dermal cells, the matrix is centered on the porous membrane and the medium is aspirated. The matrix/porous membrane is laid on top of the absorbent material. The area of the matrix is measured to the nearest 0.5 cm and the dish is reincubated. Dermal cells are harvested and counted. The density is adjusted to 3×10$^6$ cells/ml with supplemented DMEM, and about 5×10$^5$ dermal cells/cm$^2$ are inoculated onto the matrix. Supplemented DMEM is added, and the dish is returned to the incubator.

On the following day, the unit is transferred to a sterile 150 mm dish containing 25 ml of supplemental DMEM containing progesterone and epidermal growth factor, hereinafter referred to as UCMC 160. The medium is aspirated and an additional 25 ml of fresh UCMC 160 medium is added. The process is repeated daily until inoculation of epidermal cells.

Preparatory to inoculation of epidermal cells, sterile absorbent material is placed in a sterile dish saturated with UCMC 160 medium and incubated. Several hours prior to the inoculation, the previously inoculated cell/matrix/porous membrane unit is placed on top of the absorbent material. The area of the matrix is measured to the nearest 0.5 cm, and the dish is reincubated. Epidermal cells are harvested and counted. The density is adjusted to 1.2×10$^7$ cells/mi UCMC 160 medium, and the matrix is inoculated with 1×10$^6$ cells/cm$^2$, using the tip of the pipette to break the surface tension of the inoculum and make a continuous layer of epidermal cells on the inoculated matrix. After 30-60 minutes of incubation, UCMC 160 medium is added to the outside of the absorbent material. The inoculated matrix is incubated (day 0).

On day 1, the medium around the absorbent material is aspirated and fresh medium is added before reincubation. On day 2, a sterile lifting frame, consisting of wire mesh and cotton, is placed into a new sterile dish and the appropriate volume of UCMC 160 medium is added to bring the medium into contact with the wire mesh and cotton. The inoculated matrix is moved onto the lifting frame and saturated cotton, and is reincubated. The process is repeated on day 3. From day 4 onward, the process is repeated using supplemented UCMC 161 medium.

UCMC 161 medium is used for the inoculated matrix. To a base of DMEM with reduced phenol red, the following supplements (all available from Sigma, St. Louis Mo.) are added to achieve a final concentration within the ranges as indicated: strontium chloride (0.01 mM to 100 mM); linoleic acid/BSA (0.02 µg/ml to 200 µg/ml); insulin (0.05 µg/ml to 500 µg/ml); triiodothyronine (0.2 pM to 2000 pM); hydrocortisone (0.005 82 µg/ml to 50 µg/ml); a combination of penicillin (100 U/ml), streptomycin (100 µg/ml), amphotericin (0.25 µg/ml); and ascorbic acid-2-phosphate (0.001 mM to 10 mM).

To prepare UCMC 160 medium, progesterone (0.1 nM to 1000 nM) and epidermal growth factor (0.01 ng/ml to 100 ng/ml) are added to UCMC 161 medium to promote transient proliferation of keratinocytes.

Without being bound by a specific theory or mechanism, the following events likely occur. Upon inoculation, fibroblasts likely form a physiological attachment to the collagen matrix by binding via collagen-specific receptors. Because the matrix is reticulated and thus contains multiple continuous surfaces, as opposed to being perforated with direct channels or openings from a top surface to a bottom surface, the fibroblasts or other dermal cells being inoculated need not fill these channels or openings in the matrix before the epidermal cells may be added. Rather, upon inoculation, the dermal cells attach to the reticulations, and thus are able to provide a continuous surface lamination for the subsequently inoculation of epidermal cells within a shorter time period than is possible using a perforated matrix.

After inoculation, the device is incubated under conditions facilitating cell growth, maintenance, and division anywhere from less than one day (within about 16 hours to about 24 hours) up to about six weeks. The cells form a substantially continuous monolayer or multilayer surface. The device may then be transplanted into a patient, or it may be retained under these conditions until transplant. During this period, the matrix desirably degrades, cells proliferate, and new human collagen and biopolymers are deposited, all of which promote vascularization and engraftment of the device.

Engraftment of the Device

Preparatory to surgical transplantation of the device, the wound is prepared by minimizing microbial contamination and maximizing vascular supply. These conditions are usually accomplished by early (i.e., less than one week post burn) tangential excision of burn eschar to a viable base, and temporary protection of the excised wound with cadaver allograft skin or with a dermal substitute (i.e., Integra Artificial Skin®).

At the time of transplantation, the temporary component of the allograft or dermal substitute is removed to generate a highly viable graft bed with low microbial contamination. Hemostasis is attained, and one or more of the cultured skin devices are transplanted and attached with surgical staples. The device is dressed with non-adherent dressing (e.g., N-Terface®), fine-meshed cotton gauze, and bulky cotton gauze, with perforated catheters for irrigation of the device, for example, with a solution containing non-cytotoxic antimicrobial agents. Dressing changes and examination are performed on postoperative days 2 and 5, after which time the wet dressings are typically discontinued, and an appropriate antimicrobial ointment (for example, equal parts Neomycin:Bactoban:Nystatin) is applied. The ointment is applied to unhealed areas until healing is complete. Once engrafted, various agents that may facilitate the healing process and/or minimize potential complications may be applied topically to the device. For example, a nutrient solution such as a modified cell culture medium can supply nutrients to the wound during vascularization, and/or a non-cytotoxic antimicrobial solution can reduce or control microbial contamination.

The inventive device may also be used for in vitro testing. For example, the device may be used for the evaluation of compounds intended for application to the skin, such as cosmetics and/or topical therapeutic or preventative agents, or may be used for the evaluation of compounds which may contact the skin inadvertently, such as industrial chemicals and/or environmental toxins. Information derived using the inventive device for any of these agents will be beneficial in a variety of applications. As one example, it may allow determination of a single agent's, or a combination of agents', absorption, distribution, biotransformation, and elimination parameters in skin. As another example, it may allow determination of a single agent's, or a combination of agents', toxicity to one or more cell types in skin. As yet another example, it may allow qualitative and quantitative assessment of a single agent's, or a combination of agent's, uptake in skin for formulation, permeability, and dosimetry studies. As still another example, it may allow evaluation of barrier function upon insult by a single agent or a combination of agents. Other examples of applications will be appreciated by one skilled in the art. Such methods have a variety of benefits: they reduce or eliminate the need to conduct in vivo studies, they allow more controlled screening comparisons and hence provide more reproducible data, they permit administration of otherwise toxic chemicals and/or radiolabeled agents, etc. Additionally, the above-described and similar assessments may be customized by using cells from a particular individual, for example, an individual prone to allergic reactions.

Methods of using the device for in vitro testing involve, generally, preparing the device or using a prepared device, and applying the agent to the device. The agent may be applied, either directly or indirectly, to any surface of the device, and/or may be added to the medium in which the device is incubated, and/or may be added within an environment surround the device, etc. The agent may also be inoculated into the device.

A cultured skin device and method of preparing the device is thus disclosed. The inventive device and method provide treatment of skin wounds, and have structural and functional characteristics of normal uninjured skin. In one embodiment, the device contains cells from the patient to whom it is applied, thus reducing or eliminating the concern of donor compatibility. Other variations or embodiments of the invention will also be apparent to one of ordinary skill in the art from the above description. As one example, cells from non-human animals may be used to produce a device for veterinary applications. As another example, the biocompatible reticulated matrix may be acellular, or may contain only a dermal cell component, or only an epidermal cell component. As yet other examples, the epidermal cells may be only melanocytes, or the dermal cells may be only endothelial cells. Thus, the forgoing embodiments are not to be construed as limiting the scope of this invention.

What is claimed is:

1. A method to provide a physiological factor in a patient in need thereof, the method comprising, surgically preparing a skin surface to receive a skin substitute, then
providing to the prepared surface a skin substitute comprising
cultured autologous dermal cells directly attached to a biocompatible reticulated acellular matrix,
the matrix prepared from a matrix-forming collagen-containing fluid that is cast, frozen, and dehydrated,
the dermal cells providing a cellular lamination layer with cultured autologous epidermal cells directly inoculated and directly attached thereon which establishes a basement membrane between the epidermal cells and the dermal cells,
at least one of the dermal or epidermal cells bioengineered to provide a physiologic factor in the patient.

2. The method of claim 1 wherein the physiologic factor is a protein.

3. The method of claim 1 wherein the physiologic factor is insulin.

4. The method of claim 1 wherein the physiologic factor is Factor VIII.

5. The method of claim 1 wherein the physiologic factor is an angiogenic factor.

6. The method of claim 1 wherein the physiologic factor is an inflammatory process mediator.

7. The method of claim 3 wherein the patient is a diabetic.

8. The method of claim 4 wherein the patient is a hemophiliac.

9. The method of claim 5 wherein the patient is in need of enhanced vascularization.

10. A cultured skin device comprising
cultured dermal cells, wherein at least one dermal cell is selected from the group consisting of autologous cells, allogeneic cells, xenogenic cells, chimeric cells, and combinations thereof, directly attached to a biocompatible reticulated acellular matrix,
the matrix prepared from a matrix-forming collagen-containing fluid that is cast, frozen, and dehydrated,
the dermal cells providing a cellular lamination layer with cultured epidermal cells, wherein at least one epidermal cell is selected from the group consisting of autologous cells, allogeneic cells, xenogenic cells, chimeric cells, and combinations thereof, directly inoculated and directly attached thereon which establishes a basement membrane between the epidermal cells and the dermal cells.

11. The device of claim 10 wherein all dermal cells and all epidermal cells are from a single source.

12. The device of claim 10 wherein all dermal cells are from a first source, and all epidermal cells are from a source other than the first source.

13. The device of claim 10 wherein all epidermal cells are from a first source, and all dermal cells are from a source other than the first source.

14. The device of claim 10 wherein all dermal cells and all epidermal cells are autologous.

15. The device of claim 10 wherein all dermal cells and all epidermal cells are allogeneic.

16. The device of claim 10 wherein the dermal or epidermal cells are autologous, and the non-autologous cells are allogeneic.

17. The device of claim 10 wherein at least one dermal cell is autologous, and at least one epidermal cell is selected from the group consisting of autologous, allogeneic, xenogeneic, and/or chimeric.

18. The device of claim 10 wherein at least one epidermal cell is autologous, and at least one dermal cell is selected from the group consisting of autologous, allogeneic, xenogenic, and/or chimeric.

19. The device of claim 10 wherein at least one cell is genetically modified.

20. A method of producing a cultured skin device, the method comprising
isolating at least a first dermal cell from a source selected from the group consisting of autologous, allogeneic, xenogeneic, and/or chimeric dermal cells; culturing the isolated cells, and inoculating the cultured cells to a biocompatible reticulated acellular matrix, the matrix prepared from a matrix-forming collagen-containing fluid that is cast, frozen, and dehydrated, and
incubating the inoculated matrix under conditions to form at least one dermal cellular lamination layer population wherein a basement membrane is established between the dermal cells and epidermal cells directly inoculated and attached thereon, the epidermal cells from a source selected from the group consisting of autologous, allogeneic, xenogeneic, and/or chimeric dermal cells.

21. The method of claim 20 wherein all dermal cells and all epidermal cells are from a single source.

22. The method of claim 20 wherein all dermal cells are from a first source, and all epidermal cells are from a source other than the first source.

23. The method of claim 20 wherein all epidermal cells are from a first source, and all dermal cells are from a source other than the first source.

24. The method of claim 20 wherein at least one dermal cell is autologous, and at least one epidermal cell is selected from the group consisting of autologous, allogeneic, xenogeneic, and/or chimeric cells.

25. The method of claim 20 wherein at least one epidermal cell is autologous, and at least one dermal cell is selected from the group consisting of autologous, allogeneic, xenogeneic, and/or chimeric cells.

26. A pre-fabricated synthetic skin device comprising
cultured autologous and/or allogeneic dermal cells directly attached to a biocompatible reticulated acellular matrix in a sterile medium containing progesterone and epidermal growth factor,
the matrix prepared from a matrix-forming collagen-containing fluid that is cast, frozen, and dehydrated,
the dermal cells providing a cellular lamination layer for cultured epidermal cells capable of direct inoculation and direct attachment thereon to establish a basement membrane between the epidermal cells and the dermal cells,
the device stored under sterile conditions with a daily medium replacement until inoculation of epidermal cells.

27. The device of claim 26 subsequently inoculated with about $1 \times 10^6$ cells/cm$^2$ autologous or allogeneic epidermal cells and thereafter stored in a sterile medium up to six weeks.

28. A method of inoculating a biocompatible reticulated matrix with enhanced engraftment, the method comprising
inoculating fibroblasts on a biocompatible reticulated collagen matrix, the matrix prepared from a matrix-forming collagen-containing fluid that is cast, frozen, and dehydrated, the fibroblasts binding by collagen-specific receptors forming a physiological attachment to the collagen matrix by binding via collagen-specific receptors forming a continuous surface lamination layer on the matrix, and inoculating cultured epidermal cells directly on the lamination layer in a shorter time than is possible if using a perforated matrix, the epidermal cells directly attached thereon establishing a basement membrane between the epidermal cells and the fibroblasts, resulting in enhanced engraftment.

* * * * *